United States Patent [19]

Utecht

[11] Patent Number: 5,732,716
[45] Date of Patent: Mar. 31, 1998

[54] PERSONAL PROTECTION METHOD

[76] Inventor: Leo J. Utecht, 9940 Hamilton Rd., Eden Prairie, Minn. 55344

[21] Appl. No.: 453,020

[22] Filed: May 30, 1995

Related U.S. Application Data

[63] Continuation-in-part of Ser. No. 85,724, Jul. 6, 1993, abandoned.

[51] Int. Cl.⁶ .................................................. A61B 19/00
[52] U.S. Cl. .......................................................... 128/898
[58] Field of Search .................. 128/897–98; 602/41–43, 602/48, 52–54; 2/158, 161.6, 160, 167

[56] References Cited

U.S. PATENT DOCUMENTS

| | | |
|---|---|---|
| 3,342,182 | 9/1967 | Charos . |
| 3,384,083 | 5/1968 | Cozza et al. . |
| 3,409,010 | 11/1968 | Kron . |
| 3,428,603 | 2/1969 | Kroenke . |
| 3,520,401 | 7/1970 | Richter et al. . |
| 3,638,789 | 2/1972 | Tuszewski . |
| 3,764,539 | 10/1973 | Cochardt et al. . |
| 3,870,150 | 3/1975 | Hummel . |
| 4,006,116 | 2/1977 | Dominguez . |
| 4,039,629 | 8/1977 | Himes et al. . |
| 4,041,103 | 8/1977 | Davison et al. . |
| 4,065,826 | 1/1978 | Hough . |
| 4,071,921 | 2/1978 | Jury . |
| 4,347,931 | 9/1982 | Ginger et al. ................................. 2/158 |
| 4,386,179 | 5/1983 | Sterling . |
| 4,481,323 | 11/1984 | Sterling . |
| 4,511,354 | 4/1985 | Sterling . |
| 4,613,640 | 9/1986 | Deisler et al. . |
| 4,645,251 | 2/1987 | Jacobs . |
| 4,677,697 | 7/1987 | Hayes . |
| 4,706,661 | 11/1987 | Barrett . |
| 4,741,565 | 5/1988 | Bagg . |
| 4,768,818 | 9/1988 | Kolic . |
| 4,788,733 | 12/1988 | Lerner . |
| 4,844,293 | 7/1989 | McLaughlin . |
| 4,845,781 | 7/1989 | Strickland et al. . |
| 4,902,283 | 2/1990 | Rojko et al. . |
| 4,917,238 | 4/1990 | Schumacher . |
| 4,937,881 | 7/1990 | Heise ............................................. 2/158 |
| 4,951,815 | 8/1990 | Ulbrich . |
| 4,959,881 | 10/1990 | Murray . |
| 4,964,188 | 10/1990 | Olson . |
| 5,006,339 | 4/1991 | Bargery et al. . |
| 5,065,863 | 11/1991 | Moyet-Ortiz . |
| 5,112,900 | 5/1992 | Buddenhagen et al. . |
| 5,117,981 | 6/1992 | Crawford et al. . |
| 5,149,159 | 9/1992 | Bardes . |
| 5,301,806 | 4/1994 | Olson . |
| 5,310,402 | 5/1994 | Rollband . |
| 5,317,760 | 6/1994 | Best . |
| 5,407,715 | 4/1995 | Buddenhagen et al. . |

FOREIGN PATENT DOCUMENTS

| | | |
|---|---|---|
| 2 637 924 | 10/1988 | France . |
| 2 834 801 | 9/1978 | Germany . |
| 92/21401 | 12/1992 | WIPO ........................... A61M 35/00 |

OTHER PUBLICATIONS

Kraton™ Thermoplastic Rubber Typical Properties 1992—Shell Chemical Company SC:68–92.

(List continued on next page.)

*Primary Examiner*—John P. Lacyk
*Attorney, Agent, or Firm*—Friederichs Law Firm, PLC.

[57] ABSTRACT

A personal protection apparatus, including uniquely constructed barrier members that may be placed over the hands of the user and then be used for providing medical treatment including application of pressure or for accomplishing the cleanup, and for the cleanup, containment and disposal of infectious and hazardous materials, said personal protection apparatus of the invention being useful in effectively treating trauma victims while at the same time protecting the caregiver from infectious disease, bacteria, micro-organism, viruses, spores and other hazardous contaminants, said apparatus of the invention also being effectively used to safely apply various medicaments, pharmaceutical and other agents to burns, wounds and abrasions and to provide localized cooling to selected areas of a patient's body, said apparatus of the present invention being adapted to remain with the patient thereby substantially limiting the spread of contamination.

38 Claims, 9 Drawing Sheets

OTHER PUBLICATIONS

Differential Double–Coated Tape 9429—3M Technical Data May 1995—70–0705–7633–8.

Removable Tapes 665/666/F–9415PC/9416/9424/9425PC—3M Technical Data Aug. 1994—70–0702–9909–7.

Kirk–Othmer Encyclopedia of Chemical Technology, 3d ed., vol. 18, 1982, 472–473, 566–569, 650–652.

Kirk–Othmer Encyclopedia of Chemical Technology, 3d ed., vol. 20, 1982, 365–369.

Richard J. Lewis, Sr., Howley's Condensed Chemical Dictionary, 12th ed., 1993, 628, 676.

Polymers–Fibers and Textiles, a Compendium, Jacqueline I. Kroschwitz ed., 1990, 306–310.

J.A. Brydson, Rubbery Materials and Their Compounds, Elsevier Applied Science, London, 1988, 326.

The Effect of UV Light and Water on Plastics and Elastomers, Library of Congress, 1994, 331–340, 341–343.

William C. Wake and David B. Wooton, Textile Reinforcement of Elastomers, Applied Science Publishers, London, 1982, 238–239.

Thermoplastic Elastomers from Rubber–Plastic Blends, S.K. De and Anil K. Bhowmick, eds., Ellis Horwood Ltd., 1990, 14–15, 20–21, 255–261.

Handbook of Elastomers: New Developments and Technology, Anil K. Bhowmick and Howard L. Stephens, eds., Marcel Dekker, Inc., 1988, 314–315, 318–320, 342–343, 353–354.

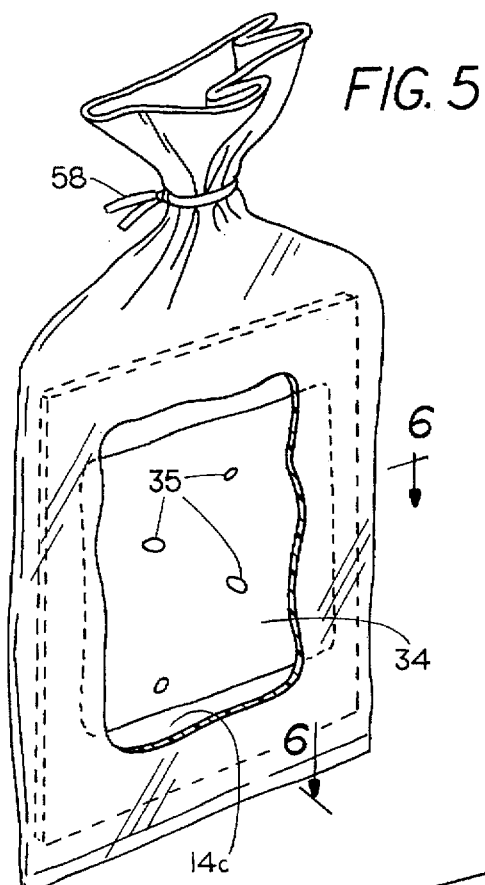
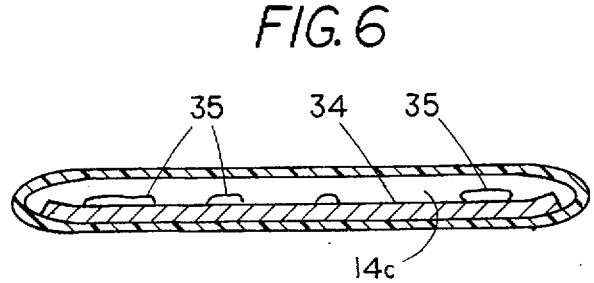
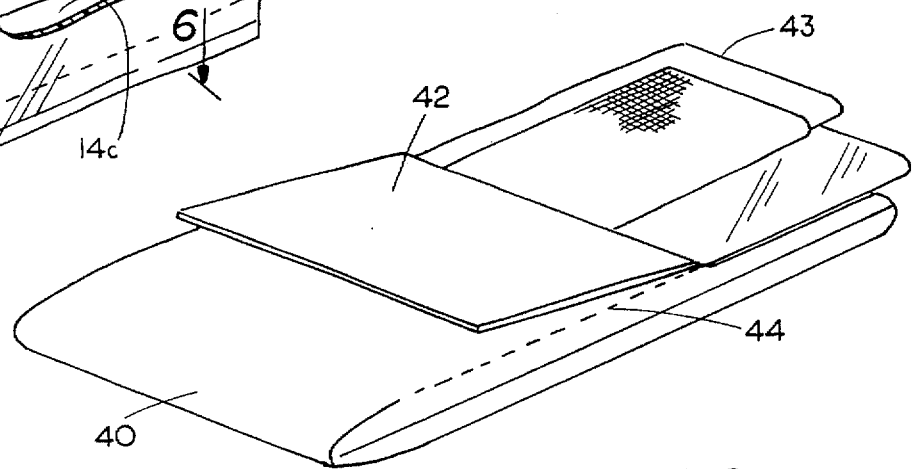
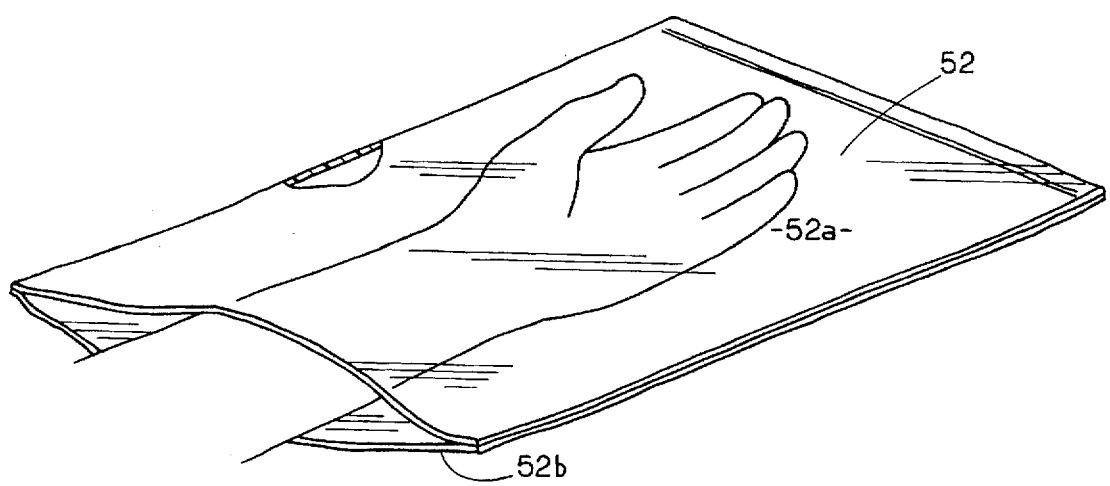

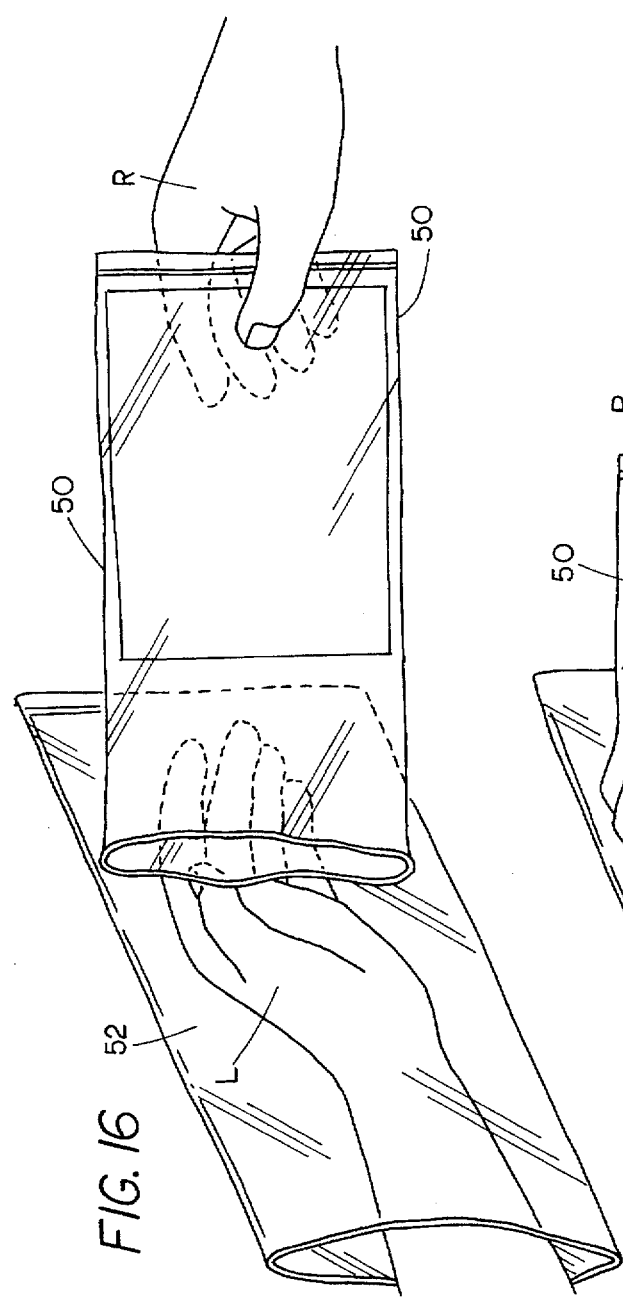
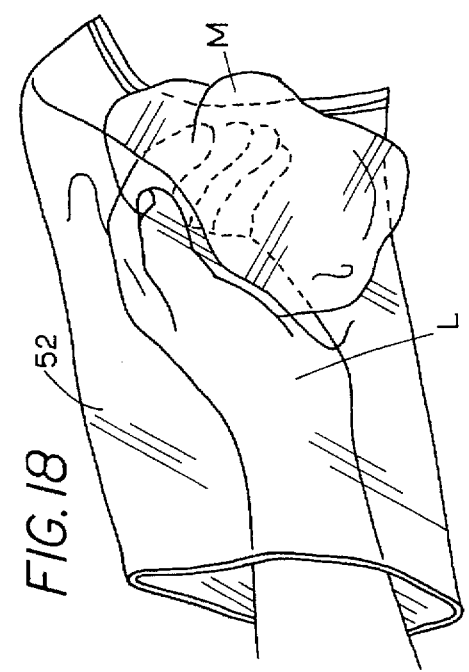
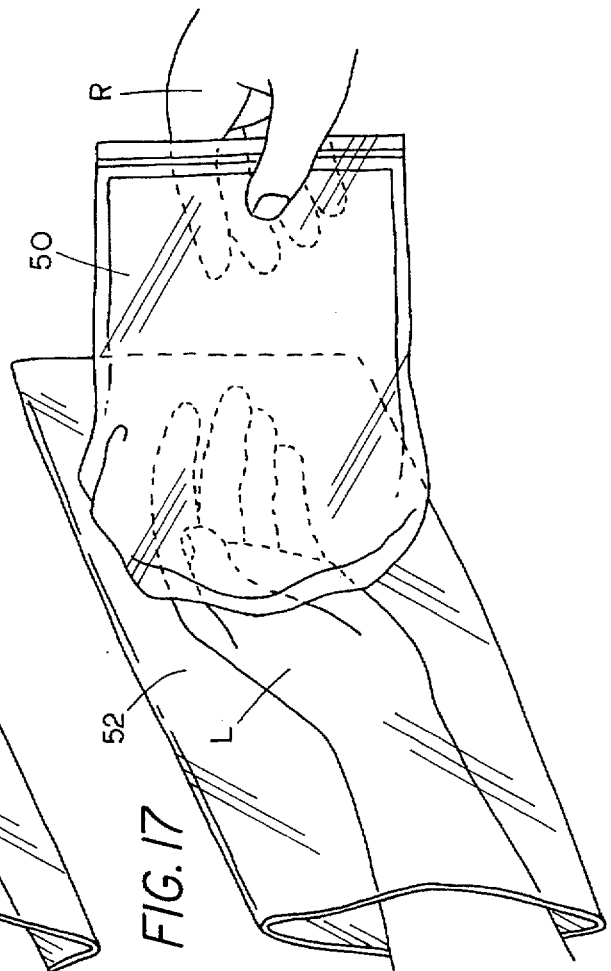
FIG. 16
FIG. 17
FIG. 18

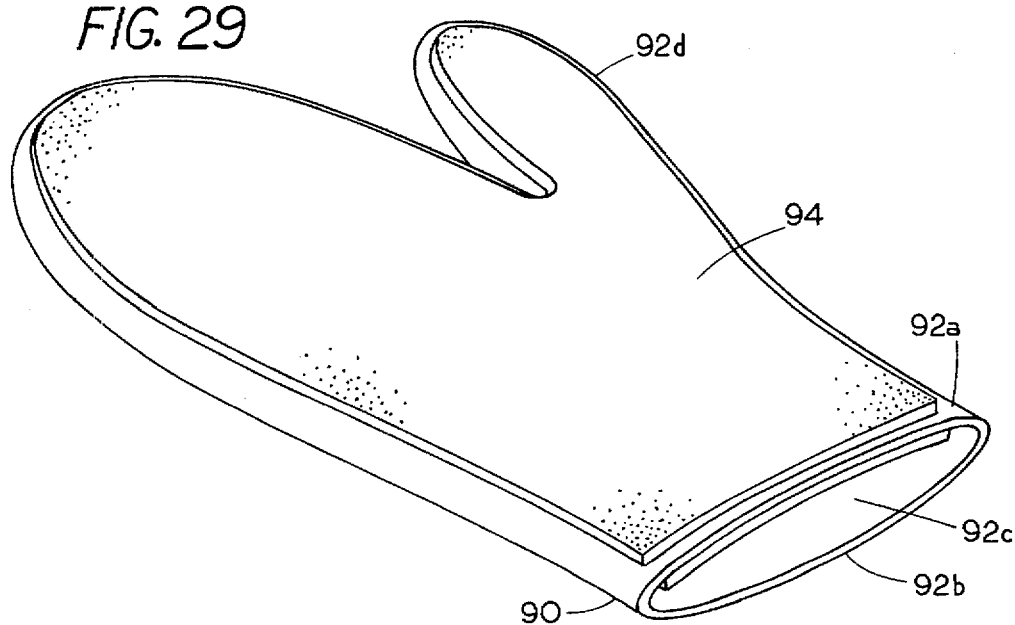
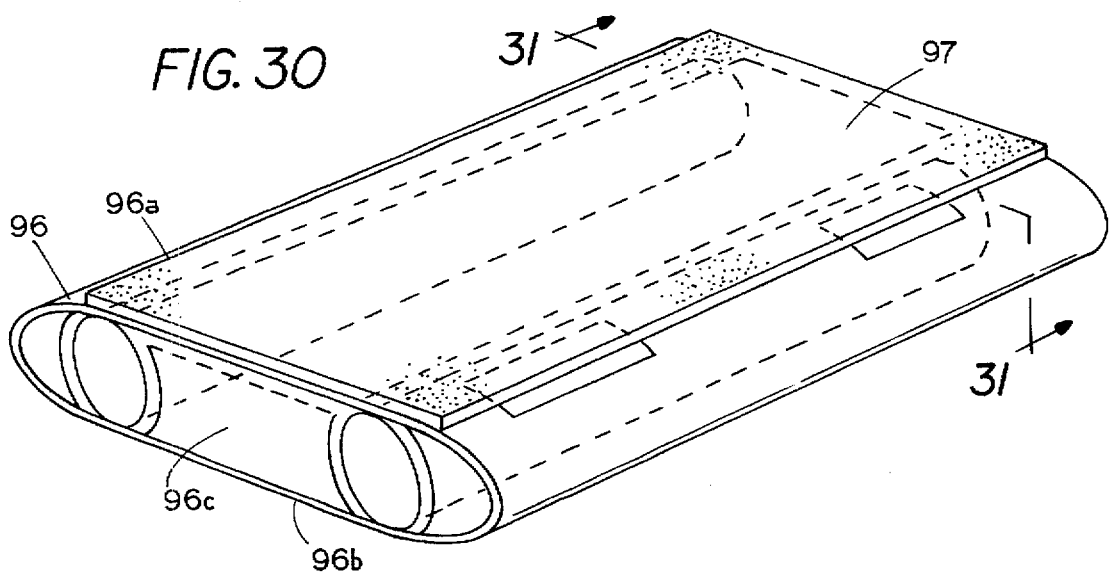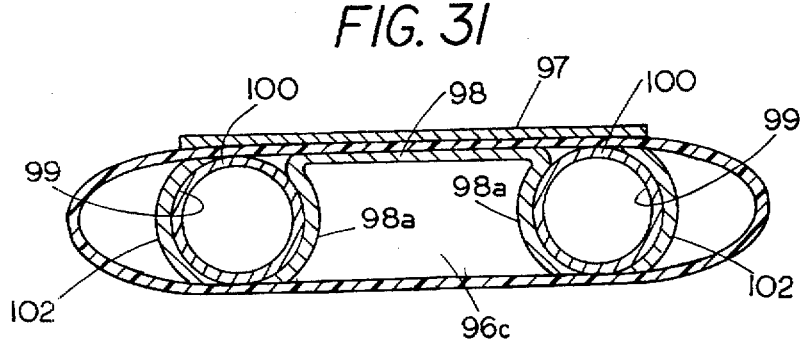

PERSONAL PROTECTION METHOD

This is a continuation-in-part of application Ser. No. 08/085,724 filed on Jul. 6, 1993 now abandoned. The parent application remains pending.

FIELD OF THE INVENTION

The present invention relates to a method for treating a wound of a human being by placing a film-like device over the wound.

BACKGROUND OF THE INVENTION

In recent years, the need for innovative methods to protect individuals from direct and/or secondary contact with dangerous materials capable of spreading infectious diseases (such as laboratory spills, human blood, body fluids, body tissue, contaminated dressings and contaminated clothing and equipment) has grown substantially. This need has grown in direct proportion to the public's increased awareness and concern that infectious diseases such as AIDS and Hepatitis A, B, C, D, and E may be contracted not only from direct contact with an infected person, but also from indirect contact with contaminated materials used in the treatment of infected persons or used in related medical research, mortuary and laboratory testing and blood banks.

In the last year alone, statistics reveal that there have been some 9000 cases of infectious disease transfer between patients and medical caregivers. Recent studies also show that sanitation workers who handle medical waste are also at substantially increased risk.

Barrier type products such as latex gloves and special biohazard disposal containers provide some protection, but studies show that currently available products are often not used and procedures are frequently not followed. This is often the case in emergency rescues and on-site first aid treatment where the increased risks of contamination are likely the greatest.

Rubber gloves (latex or vinyl), which are the most functional and widely used of current personal protection devices, have a number of troublesome drawbacks. Of primary concern is their ability to spread potentially infectious materials to equipment and people, greatly increasing the risk of secondary infection. The latex or vinyl glove is a personal protection device that typically remains with the caregiver. Once used, the glove may be slippery and contaminated with blood or other body fluids. As the caregiver moves from one patient or clean-up task to another, there are one of two undesirable alternatives; he must either attempt to leave the gloves on, risking transfer of infected materials, or take the time to remove the used gloves and replace them with clean gloves, (often three or four pairs are worn together)taking valuable time from patient care. In many medical emergencies, seconds can be critical to the patients and caregivers health.

What has long been needed is a protection device that remains with the patient, not with the caregiver. With such a device, the contaminated material is isolated and contained in one area so the treatment and clean-up job may be done faster, easier, with less cost and, most importantly, with less risk of spread of contamination.

A patient-resident device must be convenient to carry, simple to use, quick to put on and take off, and resistant to puncture. The device must be specifically designed to remain with the patient, so that the caregiver can treat other patients using other treatment devices. Additionally, the device must effectively block the transfer of fluids, viruses, spores, bacteria, or micro-organisms between caregiver and patient. At the same time, it must function in all weather extremes, provide direct medical assistance to the patient, be useful for a wide range of medical needs, and provide within the device itself the mechanism for safe biohazard containment and disposal.

In an effort to solve cross-contamination problems, a number of pouch-like devices have been suggested in the past. Many of the prior art devices are designed to be fitted over the user's hand and, after use, are designed to be turned inside out so that the cleaning surface may be encapsulated within the interior of the device.

For the most part, prior art devices fail to provide an effective barrier to infectious disease, micro-organisms contained in human blood and body fluids and like contaminates. The prior art devices protect only one hand, leaving the other hand exposed to blood borne pathogens. The prior art devices cannot be turned inside out without exposing the second hand to possible contamination. The prior art also doesn't provide for application of soap, medicines, disinfectants, deodorants, etc. for medical applications.

GENERAL DISCUSSION OF THE INVENTION

The present invention relates generally to a method of applying a personal protection, mitten/mitt like device that may be placed over the hand of the user and conveniently used for the cleanup, containment, and disposal of potentially infectious blood and body fluids. More particularly, the invention concerns a method for applying a barrier type, personal protection apparatus in effectively treating trauma victims and patients with infectious diseases while, at the same time, protecting the caregiver and patient from exchange of bacteria, micro-organisms, viruses, spores and blood-borne pathogens. Other embodiments of the present method of the invention may also be used for application of medications and other substances.

By way of example, the design of the preferred embodiment of apparatus used in the present method permits applying a dressing to a wound in a manner so as to substantially avoid cross-contamination between the patient and the caregiver. The present method also uniquely permits containment, clean-up, and removal of a myriad of different types of unwanted and dangerous material without or at least reduction of the danger of spread of contamination. After clean up, the method permits the safe transport of the contaminates to a final disposal site with reduced risk of cross-contamination.

Additionally, the invention uniquely provides for a mobile method of controllably applying direct pressure, heat, or cold, to a selected site without violating the sterile dressing environment of the selected site. The unique sterile barrier construction of the method may be adjusted to substantially admit or deny air, as well as deny fluid microbes, and pathogen transfer to or from a specific site.

In one form of the method of the invention, the barrier construction is uniquely designed to permit the insertion of one or more hands by one or more individuals. This feature of the method is particularly useful when a caregiver needs assistance in holding a dressing or applying pressure on a wound, while they obtain additional equipment, provide treatment to another injury site, and treat multiple patients.

In another very unique form of the method, a pair of barriers are provided. In using this embodiment of the invention, a barrier is placed over each hand so that both hands of the caregiver may be used in providing the necessary care and treatment. With this unique method, after the treatment has been completed, the first barrier device is turned inside out to safely enclose the contaminants thereon and then, in the reversed configuration, is safely encapsulated within the second barrier while it is being turned inside out.

The present invention provides an innovative treatment and protection system that combines a wound dressing and personal protection that, unlike traditionally used rubber gloves, resides with the patient rather than with the caregiver. More particularly, the invention provides novel personal protection that effectively protects patients, caregiver, bystanders and clean-up personnel from exposure to biohazardous material of the character often encountered during emergency medical care and in patient clean-up situations.

The invention provides a method of the aforementioned character that permits quick and easy access and exit by the caregiver and the patient several times during one treatment. Multiple access and exits may be accomplished by the same or different caregivers, including the patient, and may be performed simultaneously or in sequence.

The invention provides a sophisticated care-giving system comprised of a combination mobile wound dressing and personal protection method that provides for control at all times of the movement of dangerous or undesirable fluids, viruses, spores, bacteria micro-organisms, and other materials during treatment and disposal.

The invention provides a method for applying a sterile dressing that protects the entire hand of the caregiver from any contact with any elements or micro-organisms outside the protective zone, thereby preventing cross-contamination between patients, caregivers, clothing and equipment. The invention also provides a method for the protection of equipment from contamination, such as life support equipment. The invention also provides a method to take the pulse of a patient without contacting the patient.

The invention provides a method of the character described which permits use of a single personal protection device by the same or different caregivers, without loss of protection and without increased risk of cross-contamination.

The invention provides a method to protect caregivers while wearing regular cold weather gloves or mittens. The invention provides a method to protect the caregiver by putting the device over the caregiver's gloved hand. The method will keep the fabric and contaminants of the regular glove out of the patients wound. More effective care can be provided by the caregiver because the caregiver does not have to remove their regular gloves. The caregiver's hands remain warm and therefore more useful.

The invention provides a method which uses a mobile, self-contained, substantially sterile transport medium for body parts or other materials where a generally sterile, disease-free environment is necessary or desirable. The invention also provides a method of covering the remaining stump of a detached arm or leg of a patient. The stump can be covered by the invention to prevent cross-contamination.

The invention provides a method which uses a mobile self-contained device that permits the application of pressure and/or heat or cold to a designated site without substantially violating the sterility of either the site or of the primary containment device. For example, the device will permit the application of ice or a cold pack to a burn site while the barrier protects the burn from frostbite.

The invention provides a personal protection method that uses in combination, a wound dressing and a sterilized protective pouch, to both deliver treatment and also to block the transfer of air, fluids, dirt or other selected materials, as for example, in the treatment of a sucking chest wound.

The invention provides a method for the treatment of a sucking chest wound. The film side of the barrier member of the personal protection device can be affixed to sucking chest wounds. As the film side is flexible and will not stick to the wound, air can be expelled through the wound, but upon inhalation the film will collapse against the chest and not allow air to enter through the wound.

The invention provides a method that includes use of a barrier film of preselected permeability (hydrophilic or hydrophobic) to encourage or discourage the passage or transfer of selected elements or agents through the film. The method of the invention provides a method of the character described which is particularly useful in treating patients having infectious disease, for example, in the treatment of patients having AIDS or other persons or objects where prevention of cross-contamination is desirable. The invention provides a method to limit or deny passage of selected pathogens between the wound and hazardous material. The method not only limits passage of contaminants from the patient to the caregiver, but also passage of contaminants from the caregiver to the patient.

The invention provides a method of the class described that will assist in the treatment of injury or disease by use of a sterile absorbent dressing consisting of man-made or natural fibers containing one or more of a number of pharmaceutical agents.

The invention provides a method for personal protection that includes application of a burn dressing which is suitable for use with the traditional topical application of solutions and one which also incorporates a pouch for retaining a cooling medium.

The invention provides a method for the treatment of burns. The film side or the pad side of the device can be applied to the burn. The film can be attached to an absorbent pad covered with a non-stick, porous material. The pad could also be impregnated with medications. The device can be used to cover and protect the wound from contamination. Unlike a gauze bandage that sticks to burns and leaves fibers in the wound, the pad cover or film will not stick to the wound. The method for the treatment of burns can also incorporate the use of an ice pack. When used in this way, the dressing/pad does not have to be removed for the addition of saline and gauze to effect evaporation and the cooling of the wound. Thus, this method reduces skin damage when compared to traditional treatment methods. The ice pack inserted into the pouch provides the cooling medium. The invention provides a treatment of first to third degree burns that decreases infection because the device is sterile. It allows cooling of the burn area by using ice packs or saline, thus reducing skin damage caused by retained heat. This also enhances the survivability of the burn victim by reducing the chance of shock because the victim can be cooled more quickly. The invention also provides a method to insulate the patient in general from the cold, such as in emergency care outdoors in the wintertime.

The invention provides a method for treatment of abdominal eviscerations. The device can be used pad side down with sterile water, or the device can be used film side down without sterile water. The method retains the warmth and moisture of the patient's intestines, which can otherwise take as little as 20 minutes to dry out, causing serious medical complications and requirements of surgery.

The invention provides a method of stabilizing impaled objects particularly for ambulance transport. The device can be wrapped around, for example, a knife stuck into a chest.

The invention provides a method to stop massive or gross external bleeding. The device can be applied to a wound with external pressure provided by a series of caregivers or by the patient.

The invention provides a method for the following: a) to reduce rehabilitation time by providing padding for backboards and splints, b) to dispose of bio-hazardous materials where used as a blood born pathogen bag, c) to hold body parts and protect from frostbite when kept on ice to increase possibility of reattachment, d) to collect personal items, e) to contain vomit and for possible laboratory testing, f) to provide an occlusive neck bandage, g) to pad open bone fractures, h) to provide a container for placenta and for examination by physician, i) to clean up medical trauma sites, j) to apply medications, deodorants, disinfectants, soaps, etc. k) to stabilize body parts by providing padding for the body, l) to seal a wound and keep blood from spreading, and m) other similar uses.

The invention provides a sterile or non-sterile method of the character previously described that permits the application of a pharmaceutical agent directly to a selected site so as to assist in cleaning the site, covering the site with a wound dressing and, at the same time, treating a medical condition. The method must be sterile if used in contact with human skin.

BRIEF DESCRIPTION OF THE DRAWINGS

FIG. 5 is a generally perspective view of the device in FIG. 1 after it has been moved to an inside out configuration and the access opening thereof has been sealably closed.

FIG. 6 is an enlarged cross-sectional view taken along lines 6—6 of FIG. 5.

FIG. 7 is a generally perspective view of the opened, sealed container which contains the clean-up device.

FIG. 8 is a generally perspective view of another form of combined treatment, clean-up transport and disposal device suitable for use in the invention.

FIG. 16 is an illustrative top view of the step shown in FIG. 15.

FIG. 17 is an illustrative view of the further progression of the step shown in FIG. 16.

FIG. 18 is an illustrative view of yet a further progression of the step shown in FIG. 17.

FIG. 29 is a generally perspective view of yet another form of the combined treatment, clean-up, transport and disposal device suitable for use in the present invention.

FIG. 30 is a generally perspective view of still another form of device which may be used in the method of the invention to selectively apply heat and cold to a patient.

FIG. 31 is a cross-sectional view taken along lines 31—31 of FIG. 30.

DETAILED DESCRIPTION OF THE INVENTION

Figure 1:
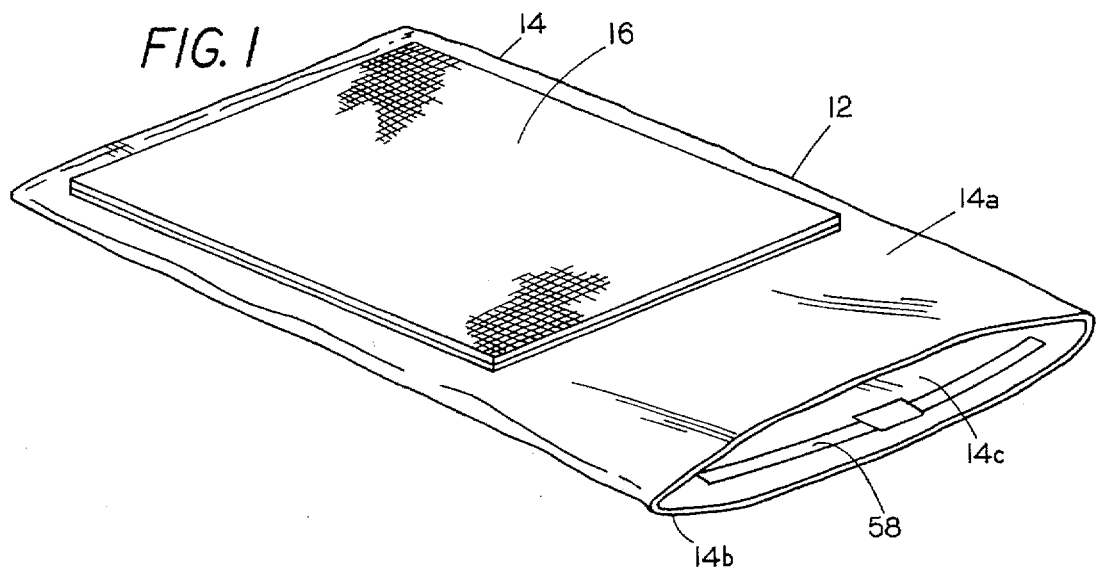
FIG. 1 is a generally perspective view of one form of the combined treatment, clean-up, transport and disposal device suitable for use in the present invention.

The present invention provides a method of treating a wounded patient by a caregiver using a barrier member having a patient-engaging surface and an interior chamber having an access opening. The method may include the steps of:

(a) inserting one or both hands of the caregiver into the interior chamber, or inserting one hand into each of two interior chamber of barrier members;

(b) placing the patient engaging surface in engagement with the patient's wound;

(c) removing the one hand of the caregiver while maintaining the patient engaging surface in engagement with the patient's wound; and (d) moving the barrier member into an inside out position to enclose the patient engaging surface therewithin.

The method may include the further steps of removing the caregiver's hand from the interior chamber and inserting therein the patient's or another caregiver's hand thereby permitting the patient or other caregiver to take over for the caregiver as the latter moves on to treat other patients. The patient's or other caregiver's hand may be removed and the caregiver's hand reinserted prior to removing barrier member from the wound and then moving the barrier member into the inside-out position.

The method of the present invention may be carried out using any of various devices such as those illustrated in the drawings, FIGS. 1 through 31. While the present invention is a method for treating a patient's wound or preparing patient for transport (stabilizing fractures, etc.), various devices will be described in detail so that the method may be better understood.

Referring to the drawings particularly to FIGS. 1 through 4, one form of the combined treatment, clean-up, transport and disposal device 12 suitable for use in the method of the present invention. The device 12 may have a barrier member 14 constructed from a thin film of microporous material that prohibits the passage therethrough of contaminants including blood-born pathogens, micro-organisms, bacteria, viruses, spores and other hazardous contaminants. The barrier member, which may be in the shape of a pouch, a glove, a gauntlet or a mitten, includes a front surface 14a and a back or bottom surface 14b which cooperate to define a hand-receiving chamber 14c. In one preferred form of the device, the barrier member 14 comprises a pouch-like enclosure which is free of pinholes and constructed of a thin film of a suitable microporous material that has pores smaller in size than 90 nanometers. The film may be devoid of pores. The film may be of any suitable polymer that will provide the necessary barrier. The thermoplastic rubber medical polymers marketed by Shell Chemical Company under the name KRATON THERMOPLASTIC RUBBER thermoplastic rubber medical polymer are suitable. These may include unsaturated mid block styrene-butadiene-styrene copolymers as well as styrene-ethylene/butylene-styrene copolymers. The polymers identified as KRATON G polymer are preferred. If a seam is present the seam should be of a similar barrier nature.

Figure 3:
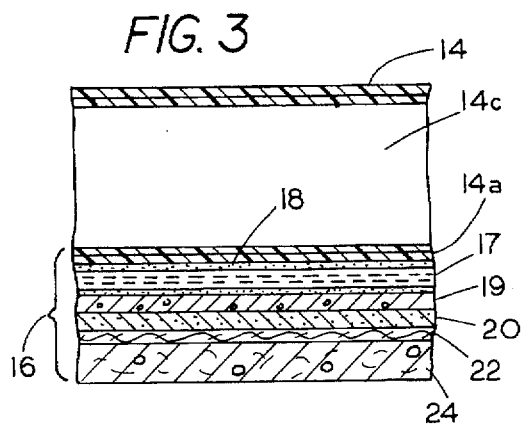
FIG. 3 is a greatly enlarged, fragmentary, cross-sectional view of the area designated by the numeral 3 in FIG. 2.

Affixed to the front surface, or face 14a of the barrier member, provide mechanism for engagement with sources of contamination including burn areas, wound areas and contaminated surfaces of various kinds. The engaging mechanism, FIGS 1 and 3, here comprises a plurality of discrete layers of material superimposed over one another. The various layers of the assemblage which comprises the engaging mechanism are collectively identified in FIGS. 1 and 3 by the numeral 16. The individual layers may exhibit various special characteristics depending upon the use that is to be made of the device. For example, some layers may comprise an absorbent material that may be a gel, a hydrogel, a hydrophobic web or a natural or synthetic fibrous material. By way of illustration, the first layer 17, which is here shown as adhesively bonded to surface 14a of the barrier member by an adhesive 18, may comprise a puncture-resistant, protective padding material, such as an elastomer, which is adapted to protect the user's hands from puncture by sharp articles such as bits of glass and the like. The next layer 18, which may be adhesively bonded to layer 17, is shown in FIG. 3 as comprising an absorbent powder packet constructed from an absorbent material such as a fabric pad or sponge. Layer 18 may contain a wide variety of powdered substances including various medicaments, beneficial agents, disinfectants, drugs and pharmaceuticals of various types. Interconnected with layer 18 is a layer 20 which is here shown as comprising a porous, cellular mass which may, for example, be an elastomer, a sponge, or a polymeric foam. Attached to member 20 is a backing member 22 to which a wound dressing such as hydrogel wound dressing 24 may be affixed in any appropriate manner.

As will be apparent from the discussion which follows, assemblage 16 may be made of a wide variety of different types of material so that the device may be used to effectively treat burns, to treat various types of wounds, to serve as an applicator of topical medications, to clean up numerous types of contaminated materials and to retrieve and safely dispose of various kinds of contaminated articles.

Similarly, assemblage 16 may be constructed and arranged to safely deal with a number of different types of contaminants in differing media, including liquids, solids, semi-solids, pastes, micro-organisms, bacteria, viruses, tissue samples and the like.

Like the engagement mechanism, the protective pouch or barrier member 12 may also be constructed in a number of different ways using a number of different types of materials. For example, the barrier may comprise a single layer of film or a combination of one or more layers of film individually layered or bonded together by heat, adhesive, chemical reaction, or numerous other attachment methods.

The film itself may be of various thicknesses and may be of metallic origin, polymeric origin, or it may be nylon, latex, rubber, polyethylene, urethane, natural or synthetic composites or any combination of these materials including materials such as Shell Oil's Kraton and any grades and derivatives thereof. This may include blends and may be of one or more layers. In summary, the materials used to construct the barrier member may be any material or combination of materials that has the property to substantially limit permeability of liquids, viruses, spores, bacteria, or micro-organisms, so long as it is acceptable for human use and preferably is lint-free and flexible under extreme temperature variations.

An example of one type of film material suitable for use in constructing the barrier member, is a material made by E. I. duPont de Nemours and Company, and sold under the name and style HYTREL polymer. Another suitable material is a material manufactured and sold by Exxon under the name and style of TPE polymer. Other basic materials acceptable for use in construction of the barrier member for certain applications include neoprene, polyethylene, polystyrenes, polysophones, polyisopene, polyvinyl, polyamide and numerous polymers including biodegradable polymers such as MYLAR polymer, latex, nylon, butyl, silicone and acetate. Materials of the character identified should preferably be of a character to provide resistance to penetration and tearing, flexibility in extreme temperature regimes, and, as previously discussed, be micro-organism impermeable. The material should malleable and stretch at cold temperatures. The device could be constructed of multiple layers of material instead of a single layer. Multiple layers could be used to avoid pin holes. Two or more layers or materials could be combined to produce different features. The layers can be sealed by electrosonic stitching mechanism without pinholes. The seal should be able withstand an extreme temperature range without pinholes. Additionally, for certain applications, it is preferable that the material be transparent or translucent and be substantially resistant to ultraviolet radiation.

It is also understood that the films used to construct the barrier member may be films or components that are coated, or impregnated with one or more chemical or pharmaceutical agents or substances capable of neutralizing or adjusting the acid or pH levels, disinfecting, deodorizing and delivering a pharmaceutical agent to the patient.

With these materials in mind and referring once again to FIG. 3, the protective absorbent pad 17 may comprise a single layer or a plurality of layers of various types of natural or synthetic materials including materials such as polyester, hydrogel, cotton, rayon, wool, nylon, silicone and like materials. Layer 17 may be bonded at either face or both faces of the barrier member 14 in any suitable manner including heat bonding, chemical bonding, adhesive bonding, electrical charge and the like.

As previously mentioned, member 18 may also be constructed from a wide variety of materials including elastomers, cellular foam and like cellular structures and may be affixed to assemblage 17 in any suitable manner.

The hydrogel wound dressing 24 may also exhibit a wide variety of special characteristics best suited for the treatment which is to be provided to the patient using the device of the invention.

Figure 4:
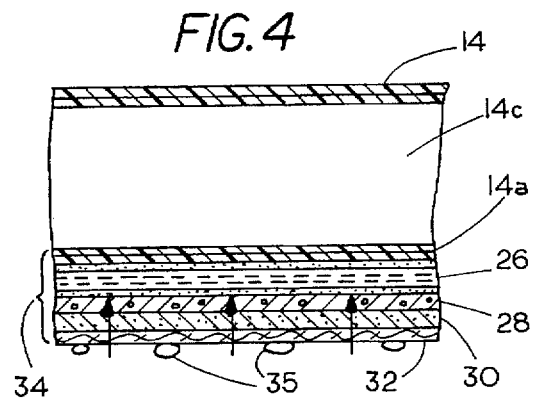
FIG. 4 is a cross-sectional view similar to FIG. 3 but showing an alternate form of engaging portion of the device and illustrating absorption of liquid and semi-solid contaminates and certain of the absorbing layers of the contaminate engaging portion.

Another embodiment of a device suitable for use in the method of the invention is shown in cross section in FIG. 4. In this form of the device, the barrier member is of similar construction to that shown in FIG. 3. Affixed to face 14a of the barrier member is an assemblage 34 which may include a plurality of layers of material of a slightly different character. More particularly, the layer designated in FIG. 14 by the numeral 26 has a protective layer which is adapted to provide protection against punctures and also is adapted to act as a cushioning material to effectively cushion the contact of the device with the patient during the treatment of a burn area, an open wound or a severe abrasion.

The device may have a laminate construction made up of a layer of sponge, a layer of gauze and a layer of absorbent material. The laminate construction may be applied to a wound. The device may include a layer of non-adherent ventilated porous wound dressing.

Affixed to layer 26 is a material layer 28 which is highly absorbent to enable it to readily absorb liquids and semi-solids in the manner illustrated by the arrows in FIG. 4. Layer 30, which is suitably affixed to layer 28 is also constructed of an absorbent material such as a sponge or foam. The outer layer of material 32 which is affixed to layer 30 is specifically adapted to engage and capture debris including solid contaminants and various other types of particulate matter of the character identified in FIG. 4 by the numeral 35.

These particulate contaminants may comprise both common materials such as sand, dirt and grit and more exotic materials such as unwanted and dangerous chemical and radioactive substances. The plurality of layers 26, 28, 30 and 32 which make up the assemblage 34 shown in FIG. 4 may contain medicaments, pharmaceuticals, disinfectants and the like in either powder or liquid form.

In practice, the device may be provided with a wide variety of identification indicia such as color coding, bar coding and like coding to identify the intended uses of the particular device and to designate the types of medicaments and pharmaceuticals contained within the engaging mechanism. Other medical coding of the devices may be accomplished through the use of various schemes well known in the art such as striping and other marking indicia which are preferably correlatable with use instructions and content labels provided on packaging containers used to package the device of the invention.

An exemplary packaging container 40 is shown in FIG. 7. This container is adapted to maintain the pre-sterilized device of the invention in a sealed, sterile environment until time of use. In the form shown in FIG. 7, the container or packaging device is provided with a flap portion 42 which may be peeled back at time of use along perforated lines 44 to expose the device of the invention which is generally designated in FIG. 7 by the numeral 43. Container 40 is preferable fabricated from a paper or plastic film material which may be positively sealed to maintain the sterile integrity of the device used in the present invention until time of use. It is to be understood that a number of different kinds of containers may be used to package the device and maintain it in a sterile environment including boxes, tubes, vials, foils and like construction.

Figure 2:
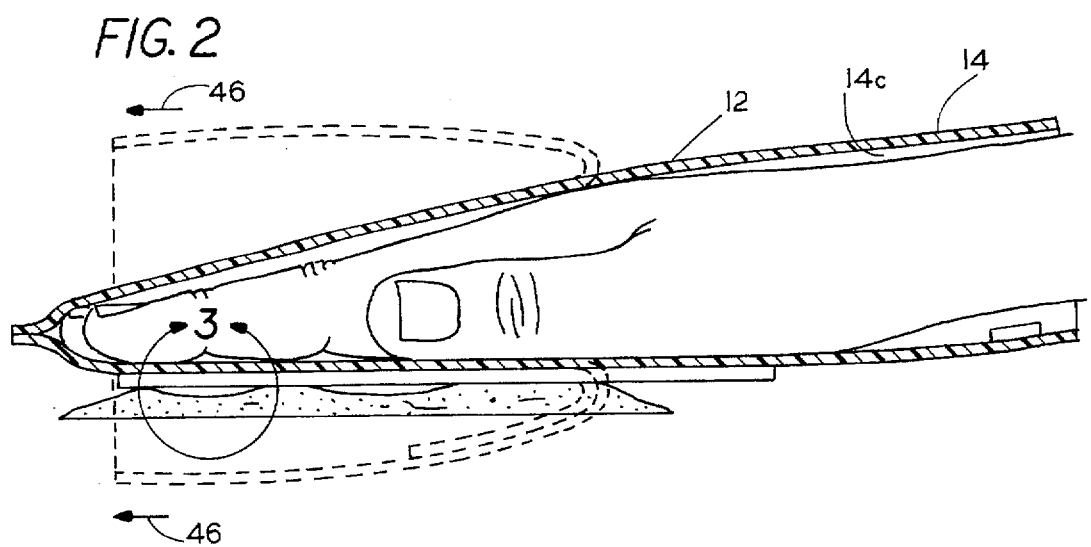
FIG. 2 is an enlarged, side-elevational, cross-sectional view of the device shown in FIG. 1. The phantom lines in FIG. 2 illustrate movement of the barrier member of the device into an inside out position.

Turning now to FIG. 2, the phantom lines shown in the drawing and the arrows associated therewith indicate the method of moving the barrier 14 into an inside out configuration so as to enclose within an interior chamber thus formed, the contaminates which have been captured by the engaging mechanism. As is apparent by a study of FIG. 2, as the barrier member 14 is moved in the position in the direction of the arrows 46, it will be turned inside out into a configuration illustrated in FIGS. 5 and 6 wherein the contaminated engaging mechanism 34 is securely disposed within interior chamber 44 of the inside out construction in the manner shown.

After the device has been turned inside out in the manner described, the open mouth thereof is sealably closed using the closure mechanism such as an adhesive strip or a tie strip 50 which is removably carried within chamber 14c (FIGS. 5 and 6). When the device has been securely sealed, the entire unit may be safely disposed within a disposal container with the contaminates affixed to or absorbed by assemblage 34 being safely contained within the interior of the inside out barrier member.

Figure 9:
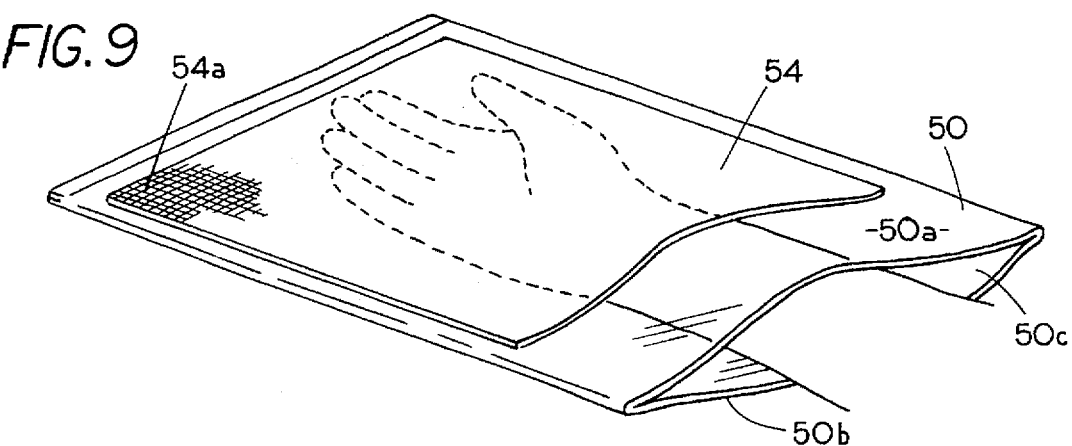
FIG. 9 is a generally perspective view of still another form of the combined treatment, clean-up, transport and disposal device suitable for use in the present invention.

Referring now to FIGS. 8, 9, 10 and 11, another form of the combined treatment clean-up, transport and disposal device of the present invention is there illustrated. In this form of the invention, two barrier members are provided. One barrier member designated by the number 50 in FIG. 9 is generally similar to the barrier member illustrated in FIG. 1 and described in the preceding paragraphs. The cooperating barrier member illustrated in FIG. 8 and designated by the numeral 52 is of a similar construction to that just described, save that in this instance, the device does not include engaging mechanism of the character previously discussed. More particularly, the device illustrated in FIG. 8 comprises a barrier member constructed from a thin film of microporous material that prohibits the passage therethrough of contaminants including infectious disease, micro-organisms and the like. The barrier member has a frontal surface 52a and a rear surface 52b. Disposed between surfaces 52a and 52b is an interior chamber adapted to receive the left hand of the care giver.

Turning particularly to FIG. 9, the barrier member of the device there shown is also preferably constructed from a thin film of microporous material that prohibits the passage therethrough of contaminants including infectious disease, micro-organisms, viruses, bacteria and the like. Barrier member 50 is provided with a frontal surface 50a to which an engaging mechanism shown here as an assemblage 54 is there affixed and a back face 50b. The front and back walls of the barrier member define an internal chamber adapted to receive the right hand of the care giver. The engaging mechanism, or assemblage 54 is similar to that previously described herein, but in this instance the outer layer comprises a wound dressing or veil generally designated by the numeral 54a. Such dressings are readily commercially available and are well known by those skilled in the art and may be removably affixed to the device in any suitable manner.

Figure 10:
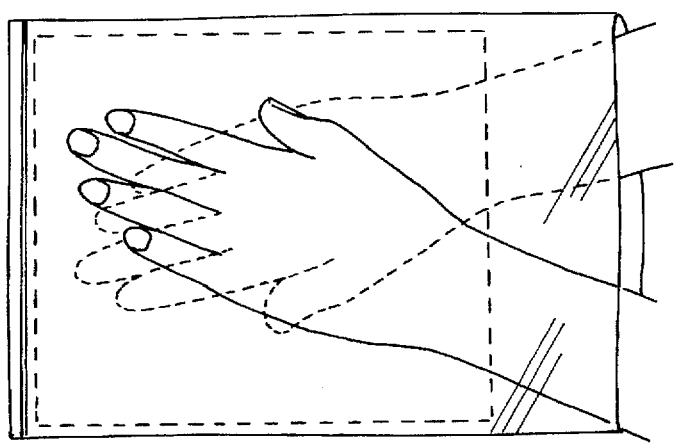
FIG. 10 is a generally illustrative view of the device of FIG. 9 showing both the care-giver's hand and the patient's hand received within the interior chamber of the device.
Figure 11:
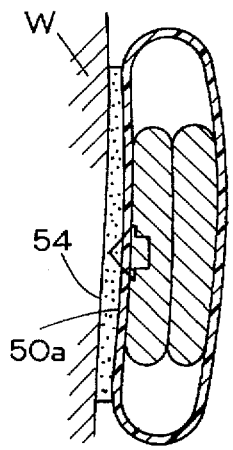
FIG. 11 is a view taken along lines 11—11 of FIG. 10.

As best seen in FIGS. 10 and 11, a unique feature of the device of this latest form of the device used in the present invention resides in the fact that the interior chamber of the device is sufficiently large to accommodate a second hand, as is illustrated in FIGS. 10 and 11, whether it be the second hand of the caregiver, the hand of the patient, or the hand of a third party bystander.

This important feature of the invention permits the caregiver to initially engage a selected area of the patient such as a wound or burn area, then have the patient insert his hand into the barrier member to maintain the engaging mechanism of the device in pressural engagement with the wound. This permits the caregiver to withdraw his hand from the device freeing it for other purposes.

When necessary, the caregiver may later reinsert his hand into the device and the patient or third party bystander may remove his or her hand therefrom. This highly important aspect of the invention permits the device to always remain with the patient rather than with the caregiver, thereby effectively preventing spread of contamination.

The provision of two units in the device of this latest form of the invention permits the accomplishment of one form of the novel methods of the invention. This method, which is illustrated in FIGS. 12 through 23 of the drawings, will now be described.

Referring to FIGS. 12 through 23, the first step in the practice of the methods of this form of the invention is for the care giver to insert his or her right hand "R" (or left hand) into the unit 50 and to insert his or her left hand into the unit 52. Using the device in the right hand, the care giver may provide treatment to the patient, perform clean up of a contaminated surface, or retrieve a contaminated article using the engaging mechanism or assemblage 54 as the area of contact.

Figure 12:
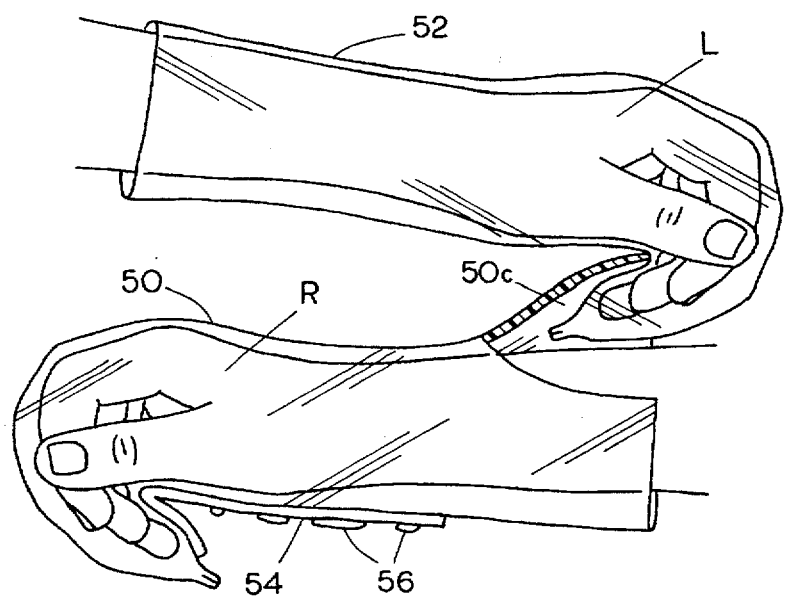
FIG. 12 is a generally illustrative view of one step in one of the methods of the invention for turning one of the devices inside out.

When the contaminants, be they liquid, solid, particulate, blood, tissue, or body fluids such as are generally designated in FIG. 12 by the numeral 56, are annexed to or absorbed by the assemblage 54, the left hand of the care giver is used to grasp unit 50 proximate the cuff or open end portion 50c thereof in the manner shown in FIG. 12. The left hand is then moved to the left as indicated by the arrow 57 in FIG. 13 moving barrier member 50 toward an inside out position in the manner illustrated in FIG. 13.

Figure 13:
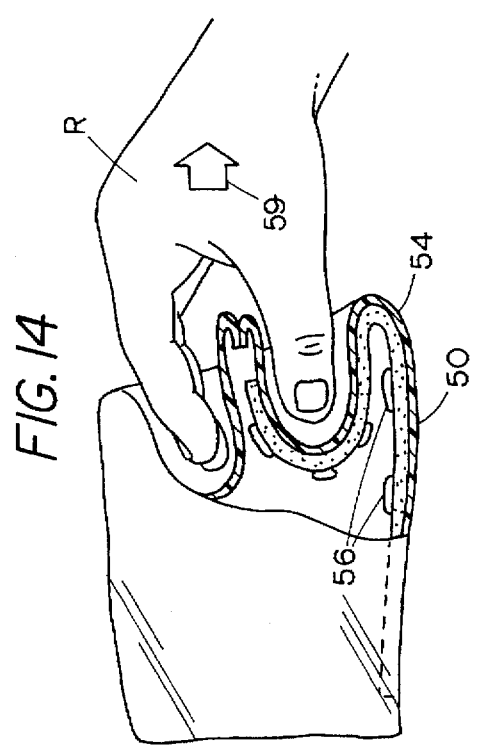
FIG. 13 is a view similar to FIG. 12 but illustrating further progress in turning one of the devices inside out
Figure 14:
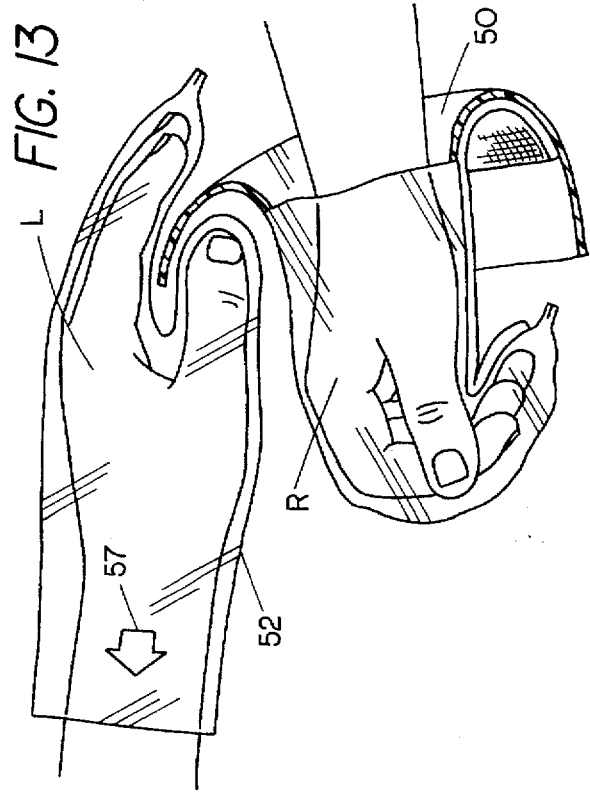
FIG. 14 is an illustrative view similar to FIG. 13 but illustrating further progression of the step of turning one of the devices inside out.
Figure 15:
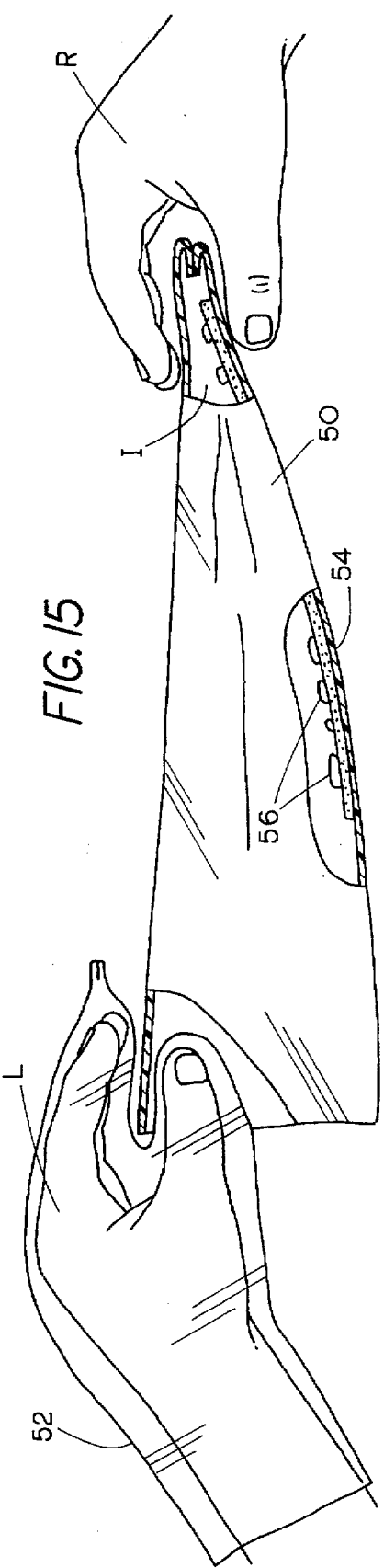
FIG. 15 is a generally illustrative view showing the first step in a method of the invention for encapsulating the first device which has been turned inside out into the second device as it is in turn turned inside out.

As the member 50 approaches the inside out configuration, the caregiver closes his hand and grips the inner walls of the device in the manner shown in FIGS. 13 and 14. At the same time, the care giver moves his right hand in the opposite direction, i.e., to the right as indicated by the arrow 59 in FIG. 14. Continued movement by the right hand will move barrier member 50 into the inside out position shown in FIG. 15. In this position, assemblage 54 along with the contaminants 56 carried thereby are enclosed within the interior of the device generally designated in FIG. 15 by the letter "T".

This done, the caregiver next moves the left hand toward the right hand which is still gripping the closed end portion of barrier member 50 and crumples the barrier member into a compacted mass identified in FIG. 18 by the letter "M". As member 50 is compressed within the closing palm of the left hand of the user's hand, of course, remains safely encapsulated within barrier member 52.

Figure 20:
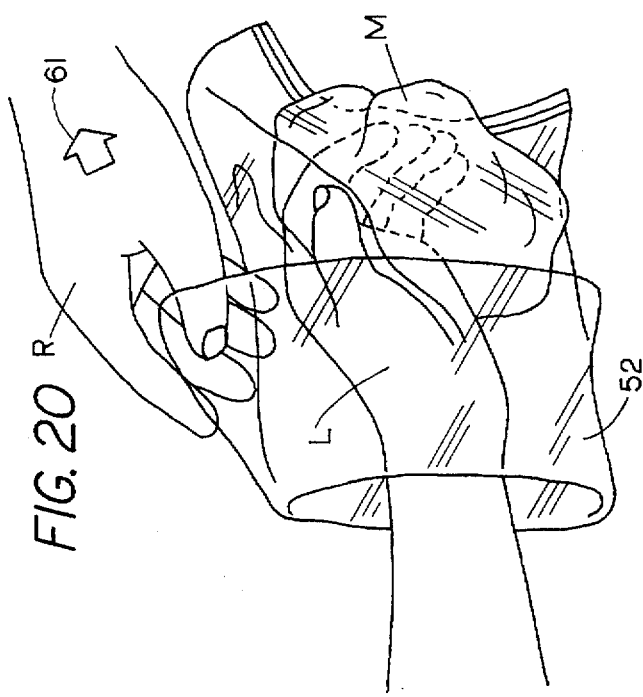
FIG. 20 is an illustrative view of the further progression of the step shown in FIG. 19.
Figure 19:
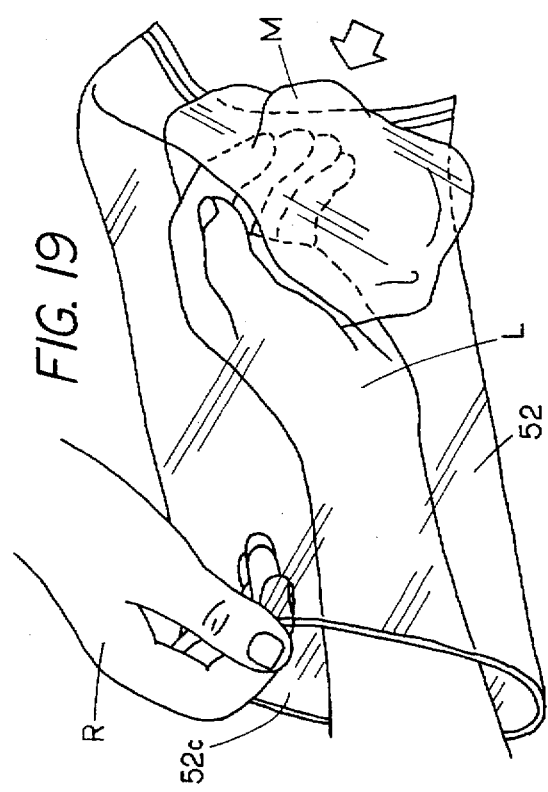
FIG. 19 is a generally illustrative view of the next step of one form of the method of the invention showing the second device being turned inside out to encapsulate therewithin the first device.
Figure 21:
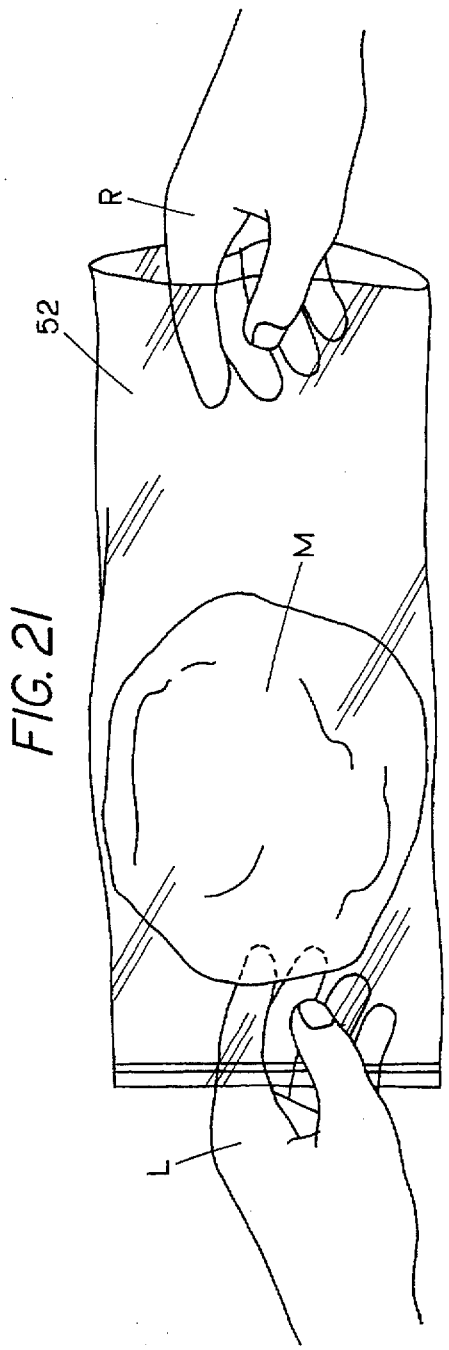
FIG. 21 is an illustrative view of the further progression of the step shown in FIG. 20.
Figure 22:
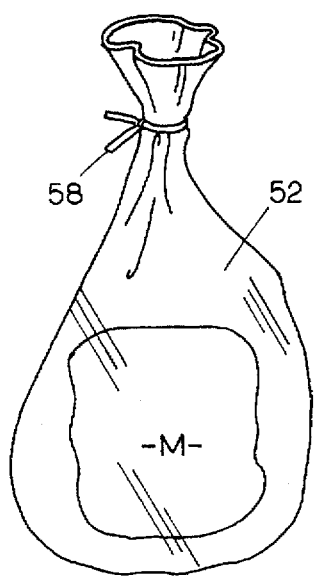
FIG. 22 is a generally illustrative view of the step of one form of the method of the invention wherein the second device is sealably closed.
Figure 23:
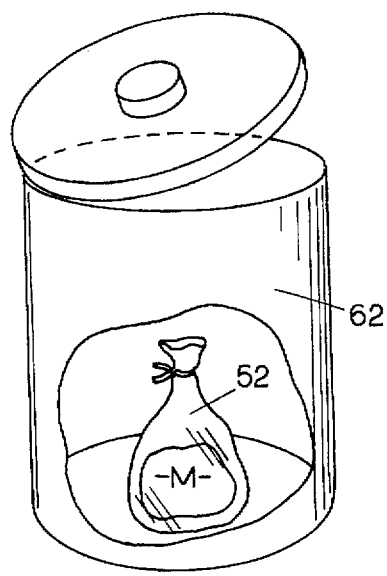
FIG. 23 is a generally diagrammatic view illustrating the final step of a method of the invention wherein the assemblage of FIG. 22 is disposed within a waste disposal container.
Figure 24:
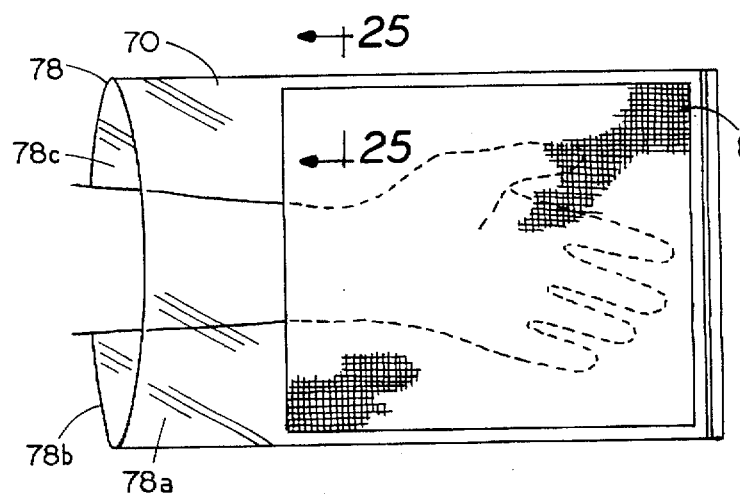
FIG. 24 is a generally plan view of yet another device that may be used in carrying out a method of the invention.

With the first barrier member 50 crumpled into the mass "M" and securely gripped within the palm of the left hand, the user uses his right hand to grip the grip barrier member 52 proximate its cuff or open end portion 52c in the manner shown in FIG. 19. As illustrated in FIG. 20, the caregiver then moves his right hand to the left in the direction of arrow 61 pulling barrier member 52 along with it so that the barrier member 52 is turned inside out in a manner to safely encapsulate the crumpled mass "M" therefrom in the manner illustrated in FIG. 21. As shown in FIG. 21, the crumpled mass "M" which comprises barrier member 50 along with assemblage 54 and the contaminates 56 carried thereby is safely encapsulated within the interior chamber of the inside out member 52. The next step in the process is then to seal the mouth or hand receiving opening of barrier member 52 with a tie strip 58 as illustrated in FIG. 22. This done, the crumpled mass is securely sealed within the interior of inside out container 52 so that the assemblage thus formed may be safely disposed of in a waste receptacle 62 in the manner shown in FIG. 23.

It is to be appreciated that at no time during the process described has the hands of the caregiver come in contact with the contaminates carried by the engaging mechanism, nor have the contaminates come in contact with any surface exterior of the handling devices.

Figure 27:
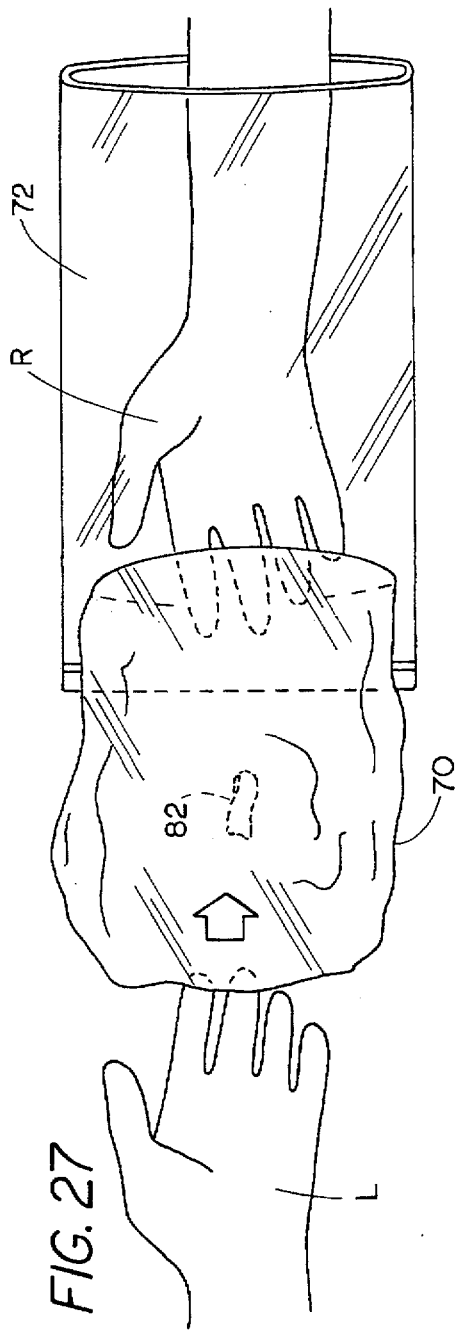
FIG. 27 is a generally illustrative view of another form of the method of the invention for encapsulating the assemblage of FIG. 26 into a second container.
Figure 28:
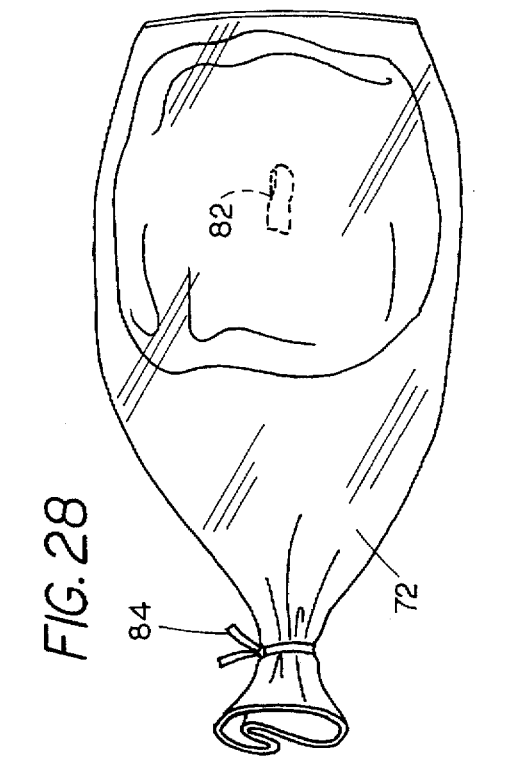
FIG. 28 is a generally illustrative view of yet a further progression of the step of the method of the invention shown in FIG. 27A.
Figure 27A:
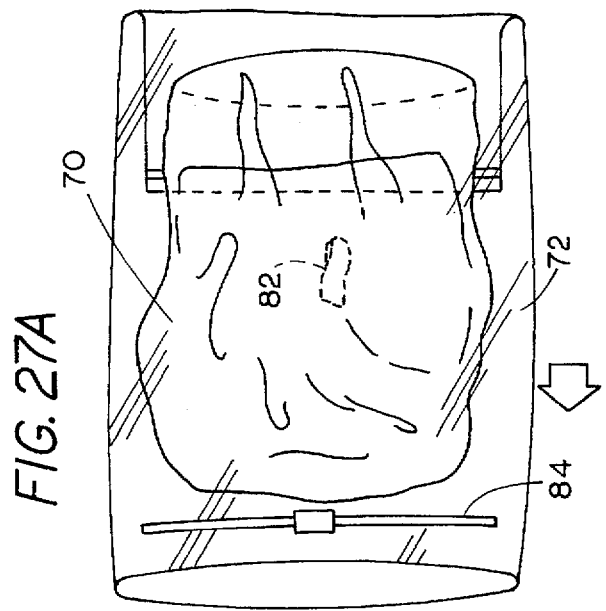
FIG. 27A is an illustrative view of the further progression of the step illustrated in FIG. 27.

Referring now to FIGS. 24 through 28, yet another form of the combined treatment, clean-up, transport and disposal device used in the present invention is illustrated. This form of the invention is similar in many respects to that just described and comprises first and second units 70 and 72 (FIG. 27). Unit 72 is of identical construction to unit 52 as described in the preceding paragraphs. Unit 70 is of similar construction to unit 50 as previously described. However, in this latest embodiment of the invention, disinfectant is provided within the interior of the device, that is within the hand-receiving chamber thereof.

Figure 25:
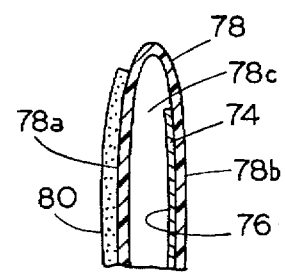
FIG. 25 is a fragmentary cross-sectional view taken along lines 25—25 of FIG. 24.
Figure 26:
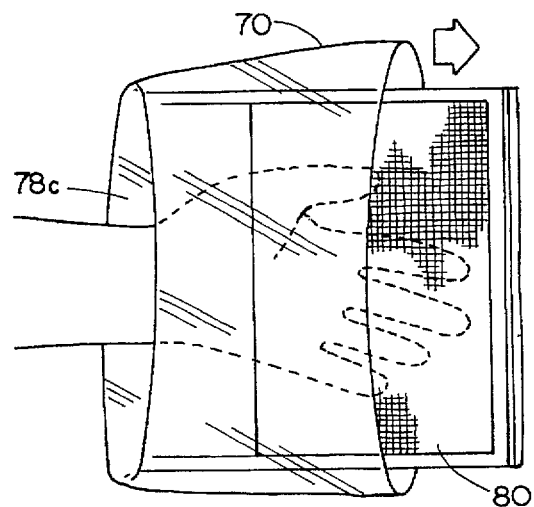
FIG. 26 is a generally illustrative view of the step of turning the device of FIG. 24 inside out.

The disinfecting mechanism, FIG. 25, comprises an absorbent pad 74 which is affixed by bonding or other suitable methods to the interior wall 76 of barrier member 78 of this form of the device used in the present invention. As before, barrier member 78 has a frontal face 78a, bottom or rear face 78b, and an interior hand-receiving chamber 78c.

Pad 74 may be constructed from a wide variety of absorbent materials of the character previously described within which a suitable disinfectant may be removably carried in liquid or powder form. Unit 70 is also provided with engaging mechanism shown here as a sponge-like, cellular member 80. Member 80 may be used as an applicator or topical medication of various types which may be carried interstitially of, or coated on, the surfaces of member 80.

While the device of this latest form of the invention may be used for various purposes including wound treatment, contamination clean up and like purposes, it is specifically designed for the retrieval of contaminated objects including human body parts, such as a severed finger, which is identified by the numeral 82 in FIG. 27. In using the apparatus of this latest form of the invention, the user's left hand is first inserted into device 70 and the right hand is inserted into device 72 in the manner shown in FIG. 27. Again, this assumes a right-handed user, the invention would work equally as well with a left-handed user. With this arrangement, the caregiver may use his left hand to apply medication to a wound area of a patient such as the patient's hands form when a finger has been severed. The left hand may then be used to retrieve the severed finger by gripping it within engaging mechanism or pad 80 and securing it within the semi-closed palm of the left hand. Device 70 is then turned inside out in the manner previously described using the right hand of the caregiver which is safely enclosed within the device 72. Once the device 70 has been turned inside out so that the body part 82 is safely contained interiorly thereof, the inside out container 70 may be crumpled and grasped within the palm of the right hand which is inserted into device 72 in the manner previously described. The left hand may then be used to turn device 72 inside out as described in the preceding section so that crumpled device 70 along with body part 82 is received within the interior of inside out device 72 as is depicted in FIG. 27. This done the tie strip 84 which has been affixed to the interior wall of device 72 may be removed and used to seal the open mouth of the barrier member of the device 72 in the manner shown in FIG. 28. This seals crumpled device 70 along with body part 82 within the interior of the inside out device 72. The body part, such as finger 82, is safely maintained within the interior chamber of device 70 which has been provided with the disinfectant mechanism or pad 74. In this way, the body part is maintained in a sealed, sterile environment within which is provided a suitable disinfectant such as the disinfectant carried by pad 76.

It is to be understood that the device, which comprises the two units 70 and 72, may be used to retrieve and safely encapsulate any number of different types of contaminated articles such as surgical instruments, syringes, drug vials, test tubes and the like. Using the device of the invention, the contaminated article may be safely placed within a controlled environment without having been touched by either hand or the user and without coming into contact with any exterior surface.

Turning now to FIG. 29 still another embodiment of the device is there illustrated. In this form, the barrier 90 is constructed in the general shape of a mitten and has frontal surface 92a, an under surface 92b, and an interior chamber 92c. Affixed to frontal surface 92a is an engaging mechanism here shown as a multi-laminate assemblage 94 which is made up of a plurality of layers of material of the general character previously described in connection with the earlier described embodiments of the invention. Accordingly, the device of the invention may be used as a clean-up device or to apply medicaments or a wound dressing to a patient. Being in the form of a mitten having a thumb receiving portion 92d, the device of this latest form of the invention is easily manipulated to accomplish certain functions including clean-up functions and for applying medicaments or other substances to a patient or to an exterior surface. Once again, barrier member 90 is preferably of a seamless construction wherein the barrier member is formed from an uninterrupted film of micro-porous material. Alternatively, the barrier member may be constructed in a manner such that the marginal portions thereof are sealably bonded together by heat sealing, abrasive or any other appropriate joining mechanism.

Being of a configuration well suited for the application of various materials to an external surface, the outer layer of assemblage 94 is preferably constructed of an absorbent material adapted to efficiently absorb liquids or semi-solids such as cleaning liquids, pastes, polishes and the like. Materials suitable for forming the exterior layer of assemblage 94 include various types of fibrous composites, polymers, polymeric foams and numerous sponge-like materials.

Turning now to FIGS. 30 and 31, yet another embodiment of the device is there illustrated. The barrier member 96 is provided in the form of a thin film, seamless construction having a frontal surface 96a, an under surface 96b, and an interior chamber 96c. The apparatus of this latest form of the device is particularly suited for selectively applying heat or cold to a selected area of a patient's body. Accordingly, provided within chamber 96c is mechanism for removably containing heating and cooling devices for selectively heating or cooling the engaging mechanism of the invention. The engaging mechanism is here shown as assemblage 97 which is affixed to the frontal surface 96a of the barrier member. The engaging mechanism, or laminate assemblage 97, is of the character previously described and is made up of a plurality of layers of material suited for the various purposes previously described herein. Also provided interiorly of chamber 96c is insulating mechanism shown here as an insulating pad 98, the purpose of which will presently be described.

As best seen by referring to FIG. 31, the device for constraining the heating and cooling mechanism comprises a pair of chambers 99 formed interiorly of chamber 96c and extending longitudinally of the barrier member. Chambers 99 are adapted to closely receive the cooling and heating mechanism which are here shown as elongated cylindrically shaped containers 100. As indicated in the drawings, chamber 99 are each formed on one side thereof by a longitudinally extending strip of insulating material 102 connected to the interior wall of the barrier member and are formed on the opposite side by portions 98a of insulating pad 98.

Heating and cooling members 100 include cylindrically shaped reservoirs within which suitable liquids may be contained, which liquids may either be controllably cooled or heated to a desired temperature prior to being inserted into chambers 99 of the device. Such heating and cooling members are well known to those skilled in the art and, in and of themselves, form no part of the present invention. Suffice to say that the heating and cooling mechanism may be liquid fillable chambers or like devices which may be inserted into chambers 99 and may function to quickly and efficiently heat and cool the engaging mechanism or assemblage 97 of the device.

In using the apparatus of this latest form of the invention, the heating and cooling cylinders 100 are either heated or cooled to the desired temperature as may be required for the treatment to be rendered and are inserted into chambers 99 which are located within interior chamber 96c of the barrier member. The user's hand is then inserted into the barrier member intermediate cylinders 100. Insulating material 98 functions to appropriately insulate the user's hand and protect it from the heat and cold generated by members 100. With the user's hand placed interiorly of chamber 90c, the engaging mechanism or pad assemblage 97 may be pressed against a selected surface of the patient's body to provide heating or cooling and also to simultaneously apply topical medications or other types of medicaments or pharmaceutical to the treatment areas as may be required.

Having now described the invention in detail in accordance with the requirements of the patent statutes, those skilled in this art will have no difficulty in making changes and modifications in the individual parts or their relative assembly in order to meeting specific requirements or conditions. Such changes and modifications may be made without departing from the scope and spirit of the invention, as set forth in the following claims.

I claim:

1. A method of providing treatment to a wounded patient by a caregiver using a barrier member having a patient engaging surface and an interior chamber having an access opening, said method comprising the steps of:

(a) inserting one hand of the caregiver into said interior chamber;

(b) placing said patient engaging surface in engagement with the patient's wound, thereby treating the patient;

(c) removing the one hand of the caregiver while maintaining the patient engaging surface in engagement with the patient's wound;

(d) removing the barrier member from engagement with the patient's wound; and (e) moving the barrier member into an inside out position to enclose the patient engaging surface therewithin.

2. The method as defined in claim 1 including the further steps of removing the caregiver's hand from the interior chamber and inserting the patient's hand therein while said patient engaging surface is in engagement with said wound.

3. The method of providing treatment to a wounded patient by a caregiver using first and second barrier members each having an engaging surface and an interior chamber having an access opening, said method comprising the steps of:

(a) inserting one hand of the caregiver into said interior chamber of said first barrier member;

(b) inserting the other hand of the caregiver into said interior chamber of said second barrier member;

(c) placing said engaging surface of said first barrier member in engagement with the patient's wound;

(d) removing the barrier member from engagement with the patient's wound;

(e) moving said first barrier member into an inside-out position to enclose said patient engaging surface thereof to form a first assemblage therewithin;

(f) grasping said first assemblage with said engaging surface of said second barrier member; and (g) moving said second barrier member into an inside-out position to enclose said first assemblage therewithin to form a second assemblage.

4. A method as defined in claim 3 including the further step of sealably closing said access opening of said second barrier member after said second barrier member has been moved to said inside-out position.

5. A method as defined in claim 4 including the further step of placing said second assemblage into a waste container.

6. A combined treatment, clean-up, transport and disposal method for use by a caregiver in rendering medical assistance to a patient, comprising:

A. inserting the hand of a caregiver in a barrier member and placing the barrier over a patient's wound and applying pressure to the wound, said barrier member being constructed from (a) a film of material that prohibits the passage therethrough of contaminates, including infectious disease micro-organisms, said barrier member having a frontal surface and an interior chamber having an access opening; (b) engaging mechanism affixed to said frontal surface of said barrier member for engagement with said wound of the patient; and B. removing the barrier member from the wound, said barrier member being moved to an inside-out position to enclose therewith said frontal surface and captured contaminates residing thereon from the wound.

7. The method as defined in claim 6 in which the hand of the caregiver and the hand of the patient is simultaneously inserted into said barrier member.

8. The method as defined in claim 7 in which said thin film is of microporous material has pores smaller in size than 92 nanometers and wherein said film is placed over a patient's wound and pressure is applied to the wound.

9. The method as defined in claim 6 in which said engaging means comprises a plurality of discrete layers of material superimposed over one another and wherein said plurality of discrete layers is placed over a patient's wound and pressure is applied to the wound.

10. The method as defined in claim 9 in which at least one of said discrete layers carries a medicament and said medicament is applied to said patient's wound.

11. The method as defined in claim 9 in which at least one of said discrete layers comprises an absorbent material and said absorbent material is placed over the patient's wound to absorb matter from said patient's wound.

12. The method as defined in claim 9 in which at least one of said discrete layers comprises a hydrogel and wherein said discrete layers are placed over the patient's wound.

13. The method as defined in claim 9 in which said interior chamber of said barrier member contains a disinfectant, and said disinfectant is applied to said patient's wound.

14. The method as defined in claim 9 further including containment means disposed intermediate said interior chamber and said frontal surface of said barrier means for removably receiving means for selectively heating and cooling said frontal surface and applying said heating and cooling means to said patient's wound to selectively heat and cool said wound.

15. A combined treatment, clean-up, transport and disposal method for use by a caregiver in rendering medical assistance to a patient, comprising:

(a) applying a seamless barrier member to a wound, said barrier member defining an enclosure having an access opening, said enclosure being adapted to simultaneously receive a hand of the caregiver and a hand of the patient, said barrier member having an enclosure wall constructed from a flexible material having a pore size less than 90 nanometers;

(b) engaging a means affixed to said barrier member with the wound of the patient during the rendering of medical assistance by the caregiver, and (c) removing said seamless barrier member from said patient and moving said seamless barrier member to an inside-out position to enclose therewithin said engaging means.

16. The method as defined in claim 15 in which said patient engaging means comprises a layer of absorbent material containing a medicament and wherein said absorbent material is applied to said wound.

17. The method as defined in claim 15 in which said patient engaging means comprises a layer of gauze and wherein said gauze is applied to said wound.

18. The method as defined in claim 15 in which said patient engaging means comprises a sponge and wherein said sponge is applied to said wound.

19. The method as defined in claim 15 in which said patient engaging means comprises a laminate construction made up of a layer of sponge, a layer of gauze and a layer of absorbent material and wherein said laminate construction is applied to said wound.

20. The method as defined in claim 15 in which said patient engaging means comprises a layer of absorbent material containing a disinfectant and wherein said absorbent material containing said disinfectant is applied to said wound.

21. The method as defined in claim 15 in which said patient engaging layer means comprises a layer of absorbent material, including a hydrogel wound dressing and wherein said hydrogel wound dressing is applied to said wound.

22. The method as defined in claim 15 in which said patient engaging means comprises a layer of non-adherent ventilated porous wound dressing and wherein said non-adherent ventilated porous wound dressing is applied to said wound.

23. The method as defined in claim 15 further including a material attached to said enclosure wall interiorly of said enclosure, said material including a disinfectant and wherein said disinfectant is applied to said caregiver's hand.

24. The method as defined in claim 15 further including means disposed within said interior chamber for removably supporting means for selectively heating and cooling said engaging means and wherein said heating and cooling means is applied to said wound.

25. A method of providing treatment to a wounded patient by a caregiver using a barrier member having a patient engaging surface and an interior chamber having an access opening, said method comprising the steps of:

(a) inserting at least one hand of said caregiver into said interior chamber;

(b) treating said patient by placing said patient engaging surface in engagement with said patient's wound; and (c) removing said at least one hand of the caregiver while maintaining said patient engaging surface in engagement with said patient's wound.

26. The method as defined in claim 25 wherein said patient's wound is a sucking chest wound.

27. The method as defined in claim 26 including the further steps of allowing air to pass out of said sucking chest wound and preventing air from entering said sucking chest wound.

28. The method as defined in claim 25 wherein said patient's wound is an abdominal evisceration.

29. The method as defined in claim 28 including the further step of placing water onto said patient engaging surface thereby providing said water in a zone between said patient engaging surface and said chest wound thereby using the water to maintain adequate moisture in the area of the intestines.

30. The method of claim 25 wherein said patient's wound is a burn.

31. The method of claim 25 including the further step of inserting a cooling means into said interior chamber to cool the burn area.

32. The method of claim 25 including the further step of re-inserting at least one hand into said interior chamber.

33. The method of claim 32 wherein said at least one hand is another caregiver's hand.

34. The method of claim 32 wherein said at least one hand is said patient's hand.

35. The method of claim 32 wherein said at least one hand is said caregiver's hand.

36. The method of claim 32 wherein said at least one hand is said caregiver's other hand.

37. The method of claim 25 wherein said at least one hand includes both of said caregiver's hands.

38. The method of claim 25 wherein said at least one hand includes one of said caregiver's hands and one of said patient's hands.

* * * * *